United States Patent [19]

Anisovich et al.

[11] Patent Number: 4,852,135
[45] Date of Patent: Jul. 25, 1989

[54] MULTICHANNEL X-RAY SPECTROMETER

[76] Inventors: Kliment V. Anisovich, prospekt Schorsa, 84/86, kv. 69, Leningrad; Jury I. Orekhov, naberezhnava, I5, kv. 329, Leningrad, Morskava; Eduard E. Soskin, ulitsa Dzerzhinskogo, 8/I3, kv. 7, Leningrad, all of U.S.S.R.

[21] Appl. No.: 116,531

[22] Filed: Nov. 4, 1987

[51] Int. Cl.⁴ .......................................... G01N 23/223
[52] U.S. Cl. ..................................... 378/49; 378/45; 378/83; 378/147
[58] Field of Search .................................. 378/44–46, 378/49, 50, 145, 147, 204, 82, 83

[56] References Cited

U.S. PATENT DOCUMENTS

| 2,897,367 | 7/1959 | Andermann et al. | 378/46 |
| 3,100,261 | 8/1963 | Bigelow | 378/45 |
| 4,417,355 | 11/1983 | Anisovich et al. | 378/49 |
| 4,649,557 | 3/1987 | Hornstra et al. | 378/84 |

FOREIGN PATENT DOCUMENTS

| 0108746 | 7/1982 | Japan | 378/45 |

OTHER PUBLICATIONS

Arl, USA Quantometer–72000, 1980.
V/O Techsnabexport, USSR, Portativny Avtomaticheskyt Mnogokanalyn Rentgenovsky Spktrometre Ark, Moscow 1981.

Primary Examiner—Craig E. Church
Assistant Examiner—John C. Freeman
Attorney, Agent, or Firm—Lilling & Greenspan

[57] ABSTRACT

A multichannel X-ray spectrometer includes an X-ray tube with a transmission target and a holder for a specimen placed opposite the target, and spectrometric channels arranged around the specimen. These spectrometric channels include, successively arranged downstream fluorescent X-rays of the specimen, a common inlet annular slit with a radius R, focusing analyzer crystals, outlet slits, and detectors of X-rays. The common annular slit is spaced from the reference surface of the holder to a distance h equal to 0.5 R, where R is 0.5 dD/2L, where d is the diameter of the outlet port of the transmission target, D is the diameter of the fo-fusing ring of the focusing analyzer crystals, and L is the length of one of the focusing analyzer crystals.

2 Claims, 3 Drawing Sheets

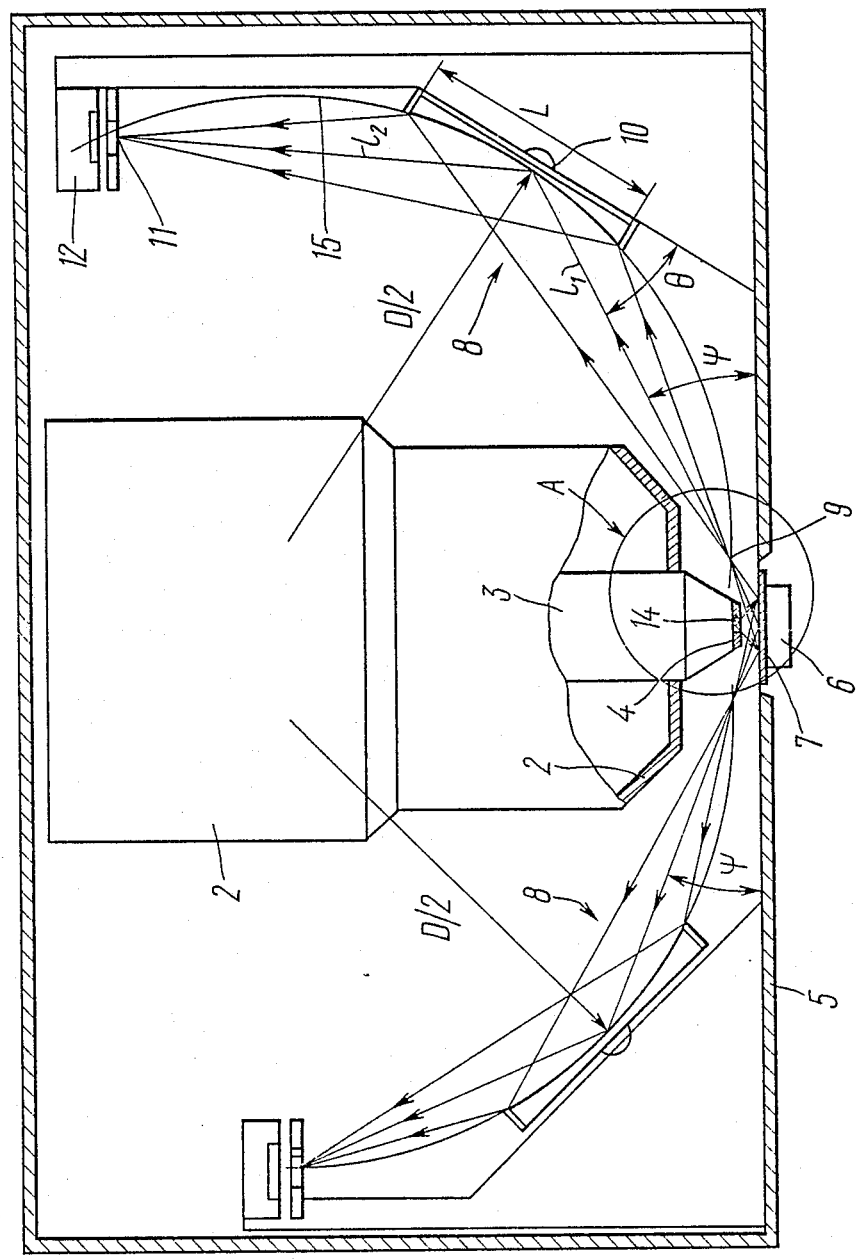

MULTICHANNEL X-RAY SPECTROMETER

BACKGROUND OF THE INVENTION

1. Field of the Invention

The present invention relates to X-ray apparatus, and more particularly it relates to multichannel X-ray spectrometers.

2. Description of the Prior Art

The invention can be used for prompt analysis of elementary compositions of substances by X-ray spectrometry techniques, e.g. in ferrous and non-ferrous metallurgy for determining the grades of and marking correspondingly various steels, brasses, iron; for sorting out materials and products, e.g. tubes, pipes, rolled sheet, plate or shapes in storage; for determining the main components and harmful impurities in intermediate and final products of mining and mineral-processing; in production of chemicals, cement or ceramics; in general engineering; in aircraft and engine engineering for analysis of engine performance; in analysis of fuels and lubricants; in medicine and biology for environment pollution control.

There is known a multichannel X-ray spectrometer which includes an X-ray tube, a holder for a specimen under investigation, facing the target of the tube, and spectrometric channels arranged about the X-ray tube and including respective inlet slits, focusing analyzer crystals, outlet slits and X-ray detectors, successively arranged in the direction of the fluorescent X-rays emitted by the specimen under investigation (ARL, USA, Quantometer—72000, 1980).

In this known spectrometer, each spectrometric channel has its own inlet slit of a rectangular shape. The distances from the target of the X-ray tube to the specimen holder and from the specimen to the inlet slits of the spectrometric channels exceed a hundred millimeters. The low relative aperture efficiency ratio of this spectrometer necessitates the incorporation of a relatively high-power X-ray tube (as powerful as 3 to 5 kW), while the design where the spectrometric channels have their own inlet slits is complicated and significantly steps up the weight and dimensions of the spectrometer (its weight being about 2000 kilograms).

There is also known a multichannel X-ray spectrometer which includes an X-ray tube with a transmission target, a holder for a specimen under investigation, facing the target of the tube, and spectrometric channels arranged about the X-ray tube and including respective inlet slits, focusing analyzer crystals, outlet slits and detectors of X-rays, successively arranged in the direction of fluorescent X-rays emitted by the specimen under investigation (V/O TECHSNABEXPORT, USSR, Portativny avtomatichesky mnogokanalny rentgenovsky spektrometr ARK, Moscow, 1981).

In this spectrometer each spectrometric channel likewise includes its own inlet slit of a rectangular shape, the inlet slits of the spectrometric channels being spaced from the specimen holder by a distance r not exceeding one fourth of the product of multiplication of the diameter D of the focusing circle of the focusing analyzer crystal by the ratio of the height H of the analyzer crystal to its length L, i.e.

$$r \leq DH/4L.$$

Owing to small distances from the target of the X-ray tube to the specimen holder and from the specimen to the inlet slits (as small as several millimeters) and to the arrangement of the inlet slits, analyzer crystals and outlet slits along a focusing circle of the diameter D, this spectrometer offers a high-efficiency aperture ratio, small dimensions and weight.

However, the design of the spectrometric channels with rectangular inlet slits would not provide for arranging about the X-ray tube an increased number of spectrometric channels (practically, in excess of six).

An increased number of spectrometric channels (e.g. twelve channels), on the other hand, can be accommodated by arranging the channels one on top of another, but this would complicate the structure of the spectrometer and increase its dimensions and weight.

SUMMARY OF THE INVENTION

It is an object of the present invention to provide more spectrometric channels in a multichannel X-ray spectrometer.

It is another object of the present invention to reduce the overall dimensions and weight of a multichannel X-ray spectrometer.

One more object of the present invention is to simplify the structure of a multichannel X-ray spectrometer while retaining its aperture efficiency ratio.

The problem is solved by a multichannel X-ray spectrometer comprising an X-ray tube with a transmission target, a holder for a specimen under investigation, facing the target of the X-ray tube, and spectrometric channels arranged about the X-ray tube, including inlet slits, focusing analyzer crystals, outlet slits and detectors of X-rays, successively arranged in the direction of fluorescent X-rays emitted by the specimen under investigation. In the spectrometer, in accordance with the present invention, the inlet slits of all the spectrometric channels are integrated in the form of an inlet annular slit of a radius R common to all these spectrometric channels, lying in a plane parallel with the reference surface of the holder for the specimen and spaced from this reference surface by a distance h equal to or less than 05. R, the radius R of the common inlet annular slit being selected within a range from 0.5 dD/2 L where:

d is the diameter of the outlet port of the through target of the X-ray tube,

D is the diameter of the focusing circle of the focusing analyzer crystals, and

L is the length of one of the focusing analyzer crystals.

Preferably, the inlet annular slit common to all the spectrometric channels is defined by the housing of the X-ray tube confining the outlet port of the transmission target and by the reference surface of the holder for the specimen.

The disclosed structure of a multichannel X-ray spectrometer provides for a substantially greater number of spectrometric channels (in excess of twelve), while reducing the overall dimensions and weight of the spectrometer and retaining a high aperture efficiency ratio.

BRIEF DESCRIPTION OF THE DRAWINGS

The invention will be further described in connection with its embodiments in a multichannel X-ray spectrometer, with reference being made to the accompanying drawings, wherein:

FIG. 1 is a partly broken away longitudinal sectional schematic view of a multichannel X-ray spectrometer embodying the invention;

DESCRIPTION OF THE PREFERRED EMBODIMENTS

Figure 4:
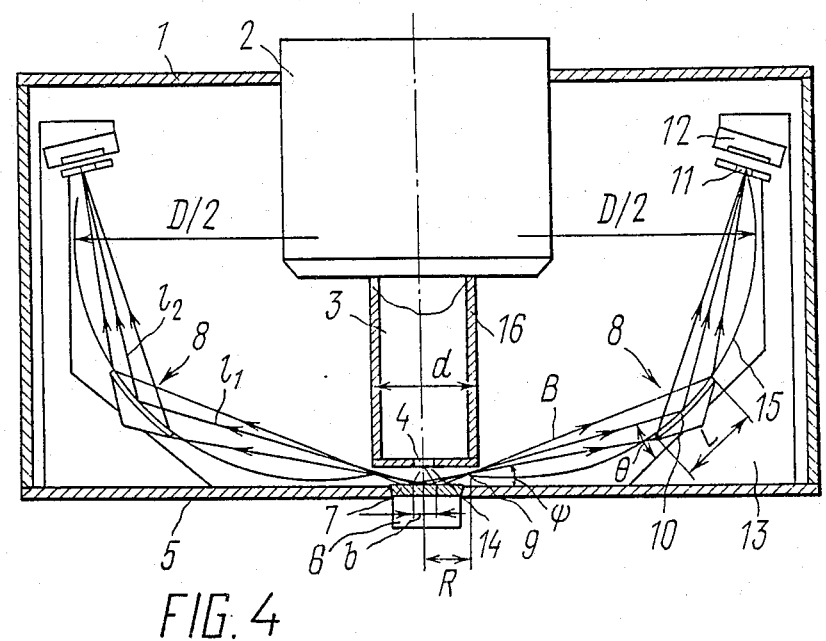
FIG. 4 is a partly broken away longitudinal sectional schematic view of a modified embodiment of an X-ray multichannel spectrometer in accordance with the invention.

The multichannel X-ray spectrometer embodying the invention comprises a housing 1 (FIG. 1) accommodating therein the housing 2 of an X-ray tube 3 with a transmission target 4. The base 5 of the housing 1 of the spectrometer accommodates a holder 6 for a specimen 7 under investigation, facing the target 4 of the X-ray tube 3. The base 5 of the housing 1 of the spectrometer serves as the reference surface of the specimen holder 6.

Arranged symmetrically about the X-ray tube 3 (FIG. 2) are spectrometric channels 8 including, successively situated in the direction B of fluorescent X-rays emitted by the specimen 7 (FIG. 1), an inlet annular slit 9 common to all the spectrometric channels 8, and respective analyzer crystals 10, outlet slits 11 and X-ray detectors 12. The analyzer crystal 10, outlet slit 11 and X-ray detector 12 of each spectrometric channel 8 are mounted on the respective bracket 13 supported, in its turn, by the base 5 of the housing 1 of the spectrometer.

The inlet annular slit 9 common to all the spectrometric channels 8 is of a radius R (FIG. 3) and situated in a plane parallel with the reference surface of the holder 6 for the specimen 7 under investigation and spaced from this reference surface by a distance h equal to or less than 0.5 R, the radius R of the common inlet annular slit 9 being in a range from 0.5 dD/2 L to dD/2 L, where:

d is the diameter of the outlet port 14 of the transmission target 4 of the X-ray tube 3, D is the diameter of the focusing circle 15 of the analyzer crystals 10, as illustrated in FIG. 1, and L is the length of one of the analyzer crystals 10.

In the embodiment being described, the common annular slit 9 (FIG. 3) lies in a plane spaced from the reference surface of the specimen holder 6 by a distance h equalling 0.5 R, while R=0.5 dD/2 L. However, as mentioned, the value of R in this embodiment can exceed 0.5 dD/2 l and be as great as dD/2 L.

Alternatively, the common inlet annular slit 9 can belong to a plane spaced from the reference surface of the specimen holder 6 by a distance h short of 0.5 R, the value of R, nevertheless, being in the range from 0.5 dD/2 L to dD/2 L.

In the embodiment of an X-ray multichannel spectrometer being described the inlet annular slit 9 (FIGS. 1 and 3) common to all the spectrometric channels 8 is defined by the housing 2 of the X-ray tube 3 confining the outlet port 14 of the transmission target 4 and the reference surface of the holder 6 for the specimen 7.

This structure of the inlet annular slit 9 (FIG. 1) common to all the spectrometric channels 8 with optimized geometric dimensions of h (FIG. 3) and R provides for increasing the number of channels in the spectrometer, while reducing its overall dimensions and weight and retaining its high aperture efficiency ratio.

Figure 3:
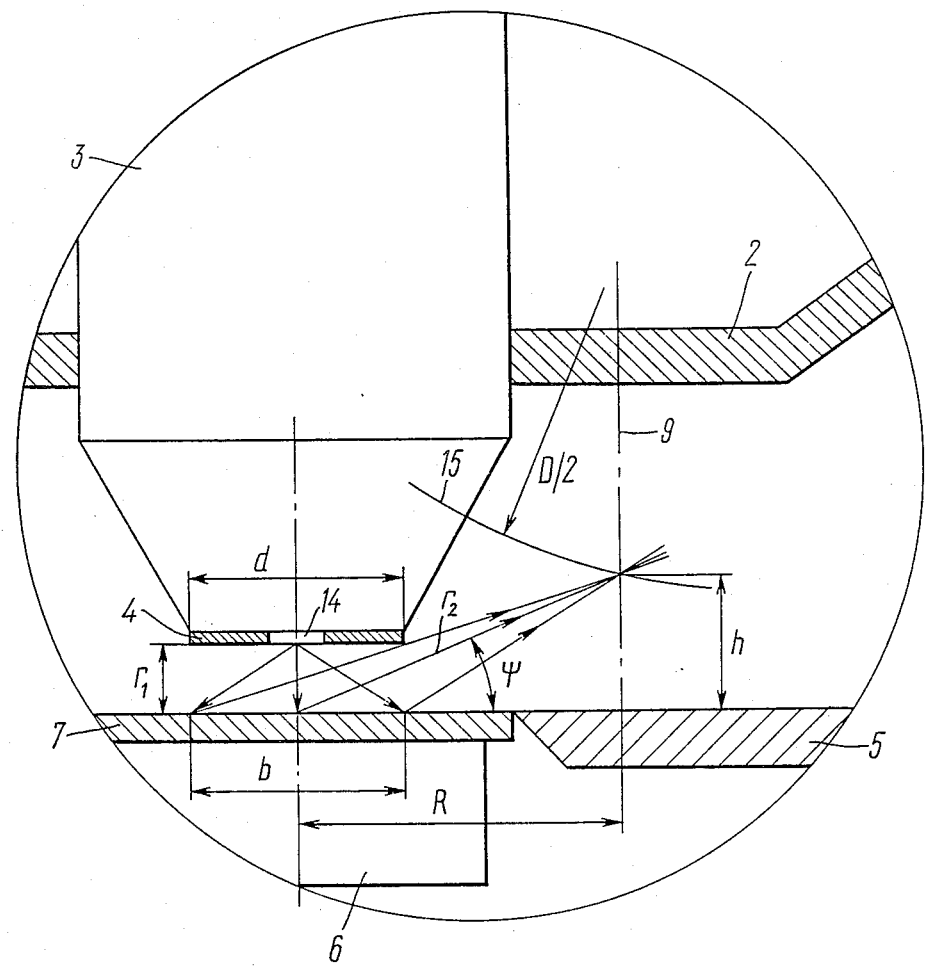
FIG. 3 shows in more detail the area A of FIG. 1.

It can be seen in FIG. 3 that the aperture efficiency ratio of the disclosed multichannel X-ray spectrometer is related to the distances $r_1$ and $r_2$, respectively, from the target 4 of the X-ray tube 3 to the specimen holder 6 and from the specimen 7 to the common inlet annular slit 9.

With the distance $r_2$ being increased, the aperture efficiency ratio of the spectrometer would not diminish as long as the diameter of the zone b of irradiation of the specimen 7 remains greater than the projection of the aperture of the analyzer crystal (L/D) upon the surface of the specimen 7, i.e. while there is maintained the ratio:

$$\frac{b \sin\psi}{r_2} \leq L/D, \quad (1)$$

where $\psi$ is the angle of reception by the analyzer crystal 10 of fluorescent X-rays emitted by the specimen 7.

On the other hand, in case of an X-ray tube 3 with a transmission target 4 with the diameter d, the effective zone b of irradiation of the specimen 7 equals 4 $r_1$, i.e. b=4 $r_1$. To maintain a high aperture efficiency ratio of the spectrometer embodying the invention, the values of $r_1$ and $\psi$ should be as small as possible. However, when the value of $r_1$ is reduced excessively, i.e. when the X-ray tube 3 is brought too close to the specimen 7, the angle $\psi$ becomes so small that the zone b of irradiation of the specimen 7 becomes "blacked out" by the transmission target 4 of the X-ray tube 3. It has been established that when the angle $\psi$ is short of 15°, the intensity of fluorescent radiation emitted by the specimen 7 drops sharply.

An optimized value of the angle $\psi$ in the multichannel X-ray spectrometer being described appears to be 20°–30°. In this range, $$r_1 = \frac{d \sin\psi}{2} = d/4 \text{ as } \sin 30° = 0.5,$$

i.e. with d = 8 ... 10 mm, $r_1$ = 2.0 ... 2.5 mm.

Considering that b=d, expression (1) is transformed:

$$\frac{d \sin\psi}{r_2} \leq L/D. \quad (2)$$

Presuming that $r_2 = R$, $R = \frac{dD}{L} \sin\psi$, i.e. with d=8 mm, D=250 mm, L=60 mm and sin $\psi$=0.35, $R_{max}$=11.2 mm.

The optimal range of R from (2) is:

R=(0.5−1) dD/2 L (with sin $\psi$=0.5).

With R≦0.5 dD/2 L and the same values of d, D, L and sin $\psi$, the value of R either equals or exceeds 8.5 mm.

With R=0.4 dD/L sin $\psi$, i.e. with R equalling 5.2 mm or less, blacking out of the zone b of irradiation of the specimen 7 by the housing 2 of the X-ray tube 3 with the transmission target 4 begins taking an effect. The distance $r_1$ and h from the target 4 of the X-ray tube 3 to the holder 6 for the specimen 7 and from the base surface of the holder 6 to the common inlet annular slit 9 is defined by a ratio:

$$\frac{h}{R} = \frac{r_1}{d/2}.$$

With $r_1 = d/4$ and $\psi = 30°$, $h = R/2$, i.e. with $R = 5.2$ mm, $h = 2.6$ mm.

With $R \leq 5.2$ mm and $h \leq 2.6$ mm, the effect of the blacking out of the zone b of irradiation of the specimen 7 by the housing 2 of the X-ray tube 3 with the transmission target 4 reduces the flux of fluorescent X-rays emitted by the specimen 7.

With $R \geq 1.1 \, dD/L \sin \psi$, i.e. with $R \geq 12$ mm, the value of fluorescent X-rays emitted by the specimen 7 beings diminishing on account of increasing value of $r_2$ (1).

The maximum number of spectrometric channels 8 (FIG. 1) accommodative about the X-ray tube 3 is determined by the length of chords $l_1 = l_2 = D \sin \theta$ and the height H of the analyzer crystals 10.

With $l_1 = l_2 = 100$ mm, and $H = 20$ mm, $$K = \frac{2\pi D \sin\theta}{H} = \frac{6.28 \cdot 250 \cdot 0.5}{20} > 30 \text{ channels,}$$

with $\theta = 30°$ ($\theta$ being Bragg's angle for the focusing analyzer crystal 10), $\pi = 3.14$ ....

A modified embodiment of a multichannel X-ray spectrometer in accordance with the present invention is illustrated in FIG. 4. It is basically similar to the spectrometer shown in FIGS. 1 to 3.

The difference is that the inlet annular slit 9 (FIG. 4) common to all the spectrometric channels 8 is defined by the cylindrical housing 16 of the X-ray tube 3 confining the outlet port 14 of the target 4 and by the reference surface of the holder 6 for the specimen 7.

Figure 2:
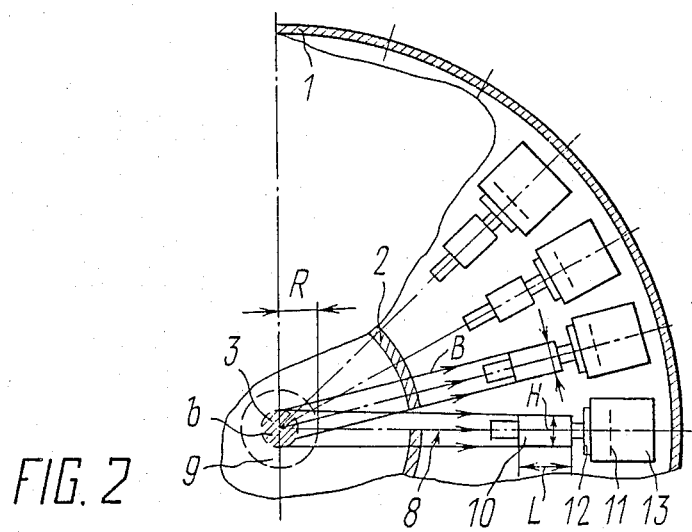
FIG. 2 is a fractional partly broken away plan view of the spectrometer illustrated in FIG. 1, with the cover removed.

The operating principle of the multichannel X-ray spectrometer embodying the present invention, illustrated in FIGS. 1 to 3, is as follows.

X-rays produced by the X-ray tube 3 (FIG. 1) with the transmission target 4 irradiate the specimen 7 under investigation, forming thereon a zone b of irradiation, as shown in FIG. 3. Fluorescent radiation emitted by the zone b of irradiation of the specimen 7 passes at an angle $\psi$ the annular slit 9 common to all the spectrometric channels 8, to fall upon their respective focusing analyzer crystals 10 set at an angle $\theta$, X-rays focused by the analyzer crystals 10 exit via the outlet slits 11 also at an angle $\theta$, to be registered by the respective X-ray detectors 12.

The multichannel X-ray spectrometer in the modification illustrated in FIG. 4 operates similarly to the spectrometer shown in FIG. 1.

The disclosed multichannel X-ray spectrometer offers a significantly increased number of accommodable spectrometric channels in a structure having small overall dimensions and weight (mere 25 kg), while retaining a high aperture efficiency ratio even when employing a relatively low-power (10 W) X-ray tube with a transmission target.

In the description of the preferred embodiment of this invention specific narrow terminology is resorted to for clarity. However, the invention is in no way limited to the terminology thus adopted and it should be remembered that each such term is used to denote all equivalent elements functioning in an analogous way and employed for similar purposes.

While this invention has been described herein in terms of preferred embodiments, it is to be understood that numerous variations and modifications may be made without departing from the spirit and scope of the invention, which is apparent to those skilled in the art.

These variations and modifications are not considered as going outside the scope and volume of the invention as set forth in the appended claims.

What is claimed is:

1. A multichannel X-ray spectrometer comprising:

a housing;

an X-ray tube having a transmission target and being disposed in said housing and emitting X-rays, said transmission target being provided with an outlet port;

a holder for a specimen, having a reference surface, said specimen being placed opposite said transmission target to accept said X-rays and fluorescing said X-rays; and spectrometric channels arranged around said X-ray tube and comprising an annular inlet slit common for all said spectrometric channels, having a radius R and transmitting said fluorescent X-rays of said specimen and positioned in a plane parallel to said reference surface of said holder and spaced a distance h equal to or less than 0.5 R from said reference surface;

focusing analyzer crystals arranged on a focusing surface directly after said common inlet annular slit in the direction of said fluorescent X-rays of said specimen in order to focus said X-radiation, said radius R of said common inlet annular slit being selected within a range from 0.5 dD/2 L to dD/2 L where d is the diameter of the outlet port of said transmission target, D is the diameter of the focusing circle of said focusing analyzer crystals, L is the length of one of said focusing analyzer crystals;

outlet slits located directly after said focusing analyzer crystals in the direction of said fluorescent X-rays of said specimen and transmitting said X-rays; and detectors of X-rays, which are located directly after said outlet slits in the direction of said fluorescent X-rays emitted by said specimen and accepting said X-rays.

2. A multichannel X-ray spectrometer as claimed in claim 1, wherein said X-ray tube has a housing; and said common inlet annular slit is formed in said housing of said X-ray tube confining said outlet port of said transmission target and said reference surface of said holder of said specimen.

* * * * *